(12) United States Patent
Taguchi et al.

(10) Patent No.: US 9,616,250 B2
(45) Date of Patent: Apr. 11, 2017

(54) TREATMENT SYSTEM, CONTROL DEVICE AND TREATMENT METHOD

(71) Applicant: KABUSHIKI KAISHA TOSHIBA, Tokyo (JP)

(72) Inventors: Yasunori Taguchi, Kawasaki (JP); Takeshi Mita, Yokohama (JP); Yukinobu Sakata, Kawasaki (JP); Tomoyuki Takeguchi, Kawasaki (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 195 days.

(21) Appl. No.: 14/329,089

(22) Filed: Jul. 11, 2014

(65) Prior Publication Data

US 2015/0018595 A1  Jan. 15, 2015

(30) Foreign Application Priority Data

Jul. 11, 2013 (JP) ................................. 2013-145631

(51) Int. Cl.
*A61N 5/10* (2006.01)

(52) U.S. Cl.
CPC ......... *A61N 5/1067* (2013.01); *A61N 5/1049* (2013.01); *A61N 2005/1061* (2013.01)

(58) Field of Classification Search
CPC .... G06T 7/20; A61N 2005/1061; A61N 5/10; A61N 5/1049; A61N 5/1048; A61N 5/1037
USPC .......................................... 600/1; 378/65–69
See application file for complete search history.

(56) References Cited

U.S. PATENT DOCUMENTS

| 6,307,914 | B1 | 10/2001 | Kunieda et al. |
| 8,345,821 | B2* | 1/2013 | Sumanaweera ...... A61N 5/1049 378/65 |
| 8,428,219 | B2* | 4/2013 | Friedrich ............... A61B 6/032 378/65 |
| 8,837,674 | B2* | 9/2014 | Ruan .................... A61N 5/1049 378/65 |
| 8,971,490 | B2* | 3/2015 | Maurer, Jr. .............. A61B 6/12 378/65 |
| 2010/0256625 | A1 | 10/2010 | Rioux et al. |
| 2012/0121068 | A1* | 5/2012 | Maurer, Jr. .............. A61B 6/12 378/62 |
| 2012/0263272 | A1 | 10/2012 | Flohr et al. |
| 2013/0101082 | A1 | 4/2013 | Jordan et al. |

FOREIGN PATENT DOCUMENTS

| JP | P3053389 | 4/2000 |
| JP | 2006-230673 | 9/2006 |

* cited by examiner

*Primary Examiner* — Samuel Gilbert
(74) *Attorney, Agent, or Firm* — Nixon & Vanderhye, P.C.

(57) ABSTRACT

According to an embodiment, a treatment system includes a plurality of first radiators, a plurality of detectors, a determiner, and a controller. Each of the first radiators irradiates a radioactive beam to a subject. Each of the detectors detects a radioactive beam transmitted through the subject and generates an image based on the detected radioactive beam. The determiner determines whether an object in the subject is included in a first region using a given image that is one of the images. The controller controls the first radiators so that, when the object is not included in the first region, a smaller amount of radioactive beams is irradiated per unit time than when the object is included in the first region.

17 Claims, 9 Drawing Sheets

TREATMENT SYSTEM, CONTROL DEVICE AND TREATMENT METHOD

CROSS-REFERENCE TO RELATED APPLICATIONS

This application is based upon and claims the benefit of priority from Japanese Patent Application No. 2013-145631 filed on Jul. 11, 2013; the entire contents of which are incorporated herein by reference.

FIELD

Embodiments described herein relate generally to a treatment system, a control device and a treatment method.

BACKGROUND

Gated radiotherapy is known for cases where the affected area of a subject moves due to the respirations, cardiac beats, intestinal movements, and the like of a subject. In the gated radiotherapy, the three-dimensional position of a marker indwelling in the affected area or near the affected area is measured and kept track of by capturing fluoroscopic views of the subject body with X-rays from two directions at given time intervals, and the affected area is irradiated with the treatment beam when the affected area or the marker enters a predetermined region.

As ways to reduce the exposure of the subject to the fluoroscopic X-ray radiation, some approaches have been known. One is to reduce the frame rate of the fluoroscopy when it is known that the movement of the affected area in the body is slow. Another is to estimate the position of a current affected area based on the positions of the same affected area measured in the past, and to omit an upcoming fluoroscopic X-ray radiation if the error between the estimated position of the affected area and the actual affected area is small.

However, the former conventional technology is incapable of reducing the amount of exposure to the fluoroscopic radiation unless the movement of the affected area in the subject body is slow. The latter requires fluoroscopic radiation from a plurality of directions to estimate the current position of the affected area, so the amount of exposure remains high.

DETAILED DESCRIPTION

According to an embodiment, a treatment system includes a plurality of first radiators, a plurality of detectors, a determiner, and a controller. Each of the first radiators irradiates a radioactive beam to a subject. Each of the detectors detects a radioactive beam transmitted through the subject and generates an image based on the detected radioactive beam. The determiner determines whether an object in the subject is included in a first region using a given image that is one of the images. The controller controls the first radiators so that, when the object is not included in the first region, a smaller amount of radioactive beams is irradiated per unit time than when the object is included in the first region.

An embodiment will now be explained in detail with reference to the appended drawings.

Figure 1:
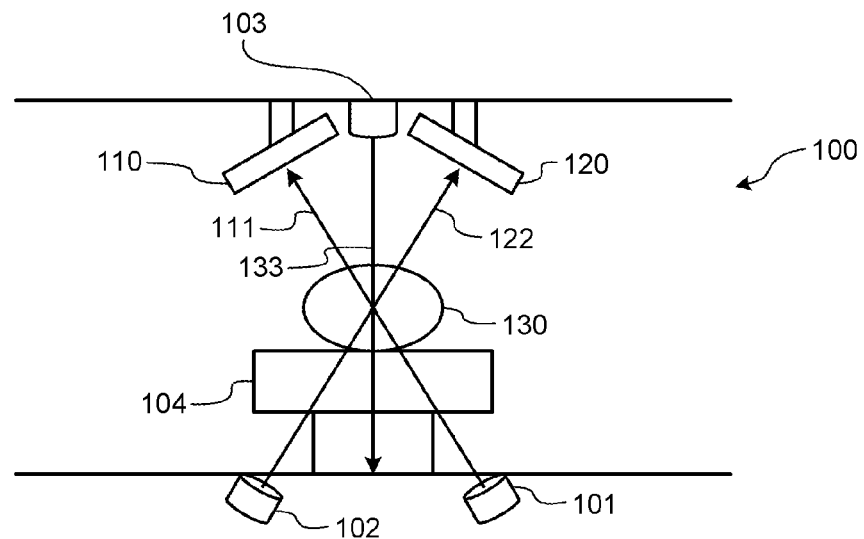
FIG. 1 is a schematic illustrating an example of a treatment apparatus according to an embodiment.
Figure 2:
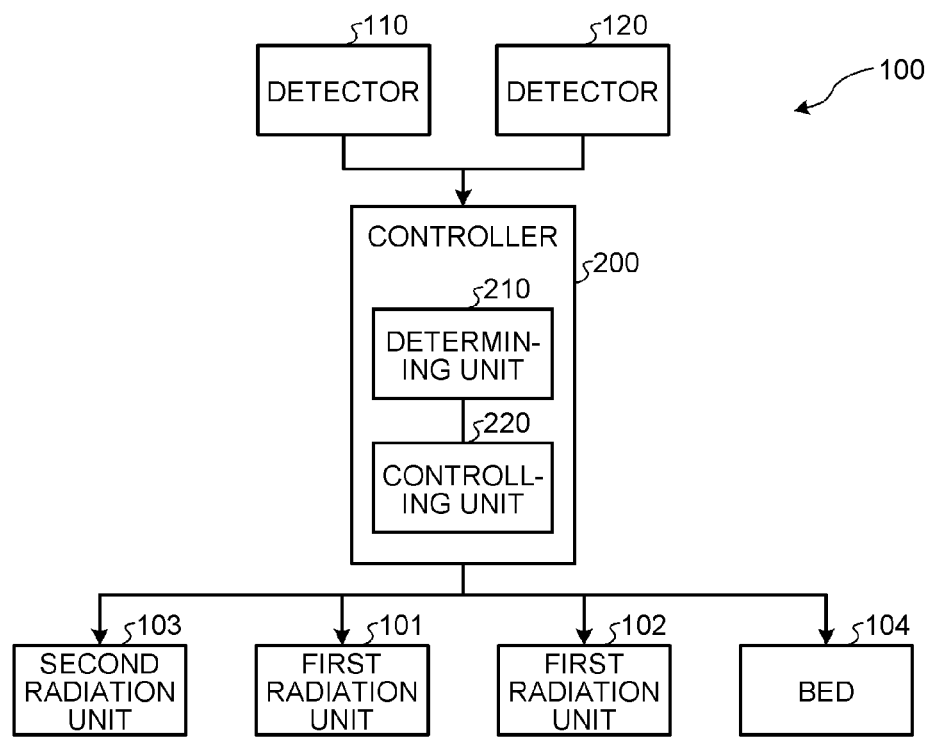
FIG. 2 is a schematic illustrating an example of a configuration of the treatment apparatus according to the embodiment.

FIG. 1 is a schematic illustrating an example of a treatment apparatus 100 according to the embodiment. FIG. 2 is a schematic illustrating an example of a configuration of the treatment apparatus 100 according to the embodiment. As illustrated in FIGS. 1 and 2, the treatment apparatus 100 includes first radiation units 101 and 102, a second radiation unit 103, a bed 104, detectors 110 and 120, and a controller 200.

The treatment apparatus 100 according to the embodiment assumes that a subject 130 lying down on the bed 104 is treated with gated radiotherapy, but the treatment performed by the treatment apparatus 100 is not limited thereto. Examples of radiotherapy include treatments using an X-ray, a gamma ray, an electron beam, a proton beam, a neutron beam, and a heavy particle beam.

Each of the first radiation units 101 and 102 (an example of a plurality of first radiation units) irradiates radioactive beams to the subject 130. In the example illustrated in FIG. 1, the first radiation unit 101 irradiates radioactive beams 111 to the subject 130, and the first radiation unit 102 irradiates radioactive beams 122 to the subject 130. The radioactive beams 111 and 122 are used for the fluoroscopy of the body of the subject 130, and may be an X-ray, for example, but without limitation. In the embodiment, the number of the first radiation units is explained to be two, but may be any number equal to or more than two.

Figure 3:
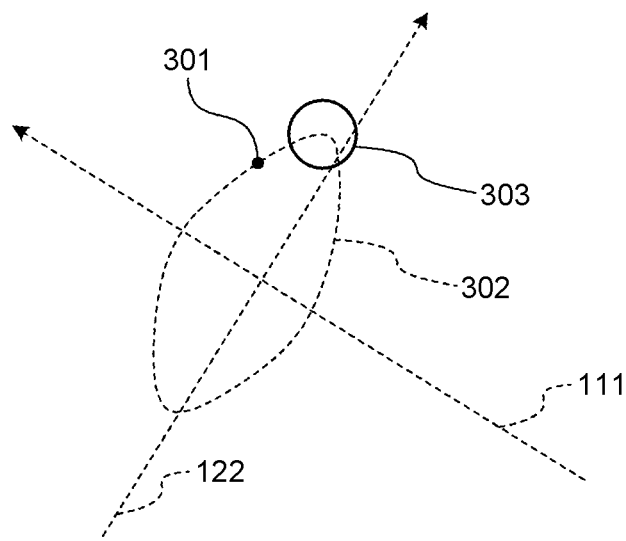
FIG. 3 is a schematic for explaining an example of the condition of a subject body according to the embodiment.

FIG. 3 is a schematic for explaining an example of the condition of the body of the subject 130 according to the embodiment. In the example illustrated in FIG. 3, because of respiration, cardiac beats, and intestinal movements of the subject 130, an object 301 in the subject 130 is moving three-dimensionally along a trajectory 302. The object 301 may be an affected area of the subject 130, or a marker indwelling near the affected area. The marker may be made of any material (such as gold) not allowing the radioactive beams 111 and 122 to pass through easily. In the example illustrated in FIG. 3, the radioactive beams 111 and 122 pass through the body of the subject 130. The direction in which the radioactive beams 111 and 122 are irradiated may be any directions that are different from each other, without limitation to the directions perpendicular to each other illustrated in FIG. 3. In the example illustrated in FIG. 3, the second radiation unit 103 irradiates a treatment beam 133 to the affected area of the subject 130 while the object 301 is included in a treatment beam irradiated region 303 (an example of a second region), whereby allowing the affected area to be treated. The treatment beam irradiated region 303 is a three-dimensional region determined by a physician or the like at a time of pretreatment planning.

The detectors 110 and 120 (an example of a plurality of detectors) detect the radioactive beams transmitted through the subject, and generates images based on the detected radioactive beams. In the example illustrated in FIG. 1, the detector 110 detects the radioactive beams 111 irradiated from the first radiation unit 101, and generates a fluoroscopic image of the object in the body of the subject 130 from the detected radioactive beams 111. The detector 120 detects the radioactive beams 122 irradiated from the first radiation unit 102, and generates a fluoroscopic image of the object in the body of the subject 130 from the detected radioactive beams 122. In the embodiment, the number of detectors is explained to be two, but may be any number as long as the number is the same as the number of the first radiation units, without limitation.

Figure 4:
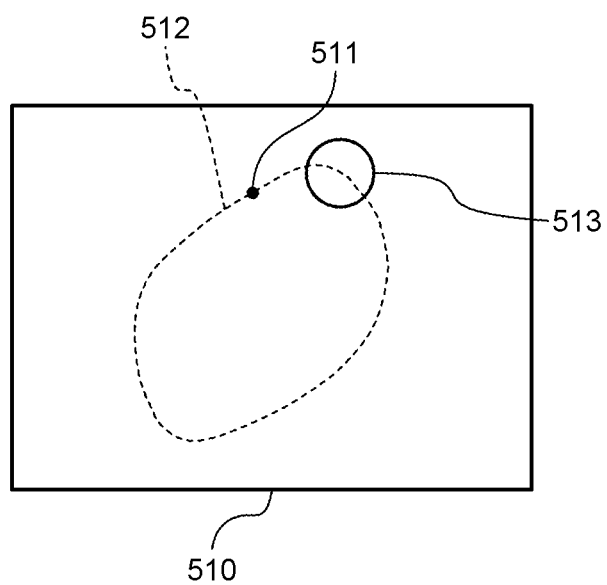
FIG. 4 is a schematic illustrating an example of an image generated by a detector according to the embodiment.

FIG. 4 is a schematic of an example of an image 510 generated by the detector 110 according to the embodiment. The image 510 includes an object image 511 that is a projection of the object 301 (see FIG. 3) on the detection surface of the detector 110 in the direction of the radioactive beams 111 irradiated. A projected trajectory 512 is a projection of the trajectory 302 (see FIG. 3) on the image 510, and a projected region 513 is a projection of the treatment beam irradiated region 303 (see FIG. 3) on the image 510. In the example illustrated in FIG. 4, the projected trajectory 512 and the projected region 513 are displayed in the image 510 just for the purpose of reference, but may not be displayed in the image 510.

Figure 5:
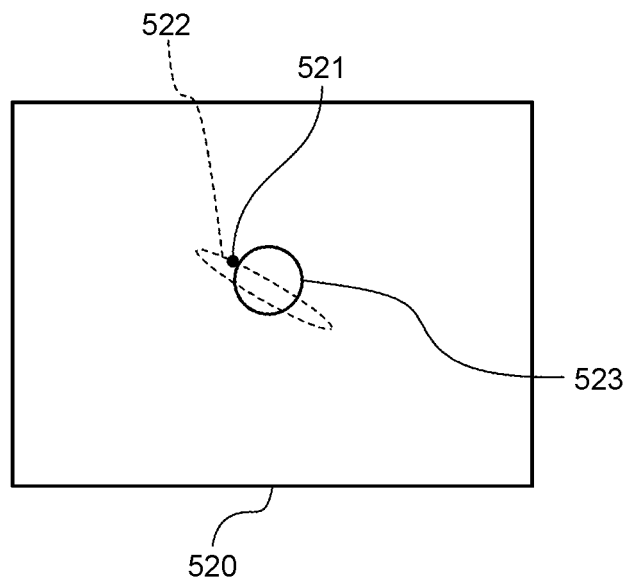
FIG. 5 is a schematic illustrating an example of an image generated by another detector according to the embodiment.

FIG. 5 is a schematic of an example of an image 520 generated by the detector 120 according to the embodiment. The image 520 includes an object image 521 that is a projection of the object 301 (see FIG. 3) on the detection surface of the detector 120 in the direction of the radioactive beams 122 irradiated. A projected trajectory 522 is a projection of the trajectory 302 (see FIG. 3) on the image 520, and a projected region 523 is a projection of the treatment beam irradiated region 303 (see FIG. 3) on the image 520. In the example illustrated in FIG. 5, the projected trajectory 522 and the projected region 523 are also displayed in the image 520 just for the purpose of reference, but may not be displayed in the image 520.

The controller 200 controls the units included in the treatment apparatus 100. The controller 200 includes a determining unit 210 and a controlling unit 220.

The determining unit 210 determines whether the object in the subject body is included in a first region using a given image that is one of a plurality of images. The given image is an image generated by one of the detectors 110 and 120 detecting one of the radioactive beams irradiated from a given direction. In the embodiment, the given direction is assumed to be fixed, but may also be changed. For example, the direction of the radioactive beams 111 irradiated may be set to the given direction at first time, and the direction of the radioactive beams 122 irradiated may be set to the given direction at second time.

Furthermore, in the embodiment, the first region is assumed to be a projection of the second region on the given image, but is not limited thereto.

As one example, consider a case in which the second region is the treatment beam irradiated region 303 (see FIG. 3), and the given image is the image 510 but not the image 520 (see FIGS. 4 and 5) (that is, the given direction is the direction of the radioactive beams 111 irradiated). In such a case, because the first region corresponds to the projected region 513, the determining unit 210 determines that the object 301 (see FIG. 3) is included in the first region if the object image 511 is included in the projected region 513 in the image 510, and determines that the object 301 (see FIG. 3) is not included in the first region if the object image 511 is not included in the projected region 513 in the image 510.

As another example, consider a case in which the second region is the treatment beam irradiated region 303 (see FIG. 3), and the given image is the image 520 but not the image 510 (see FIGS. 4 and 5) (that is, the direction of the radioactive beams 122 irradiated is the given direction). In this case, because the first region corresponds to the projected region 523, the determining unit 210 determines that the object 301 (see FIG. 3) is included in the first region if the object image 521 is included in the projected region 523 in the image 520, and determines that the object 301 (see FIG. 3) is not included in the first region if the object image 521 is not included in the projected region 523 in the image 520.

If the object is included in the first region, the determining unit 210 further determines whether the object is included in the second region using a plurality of images. For example, consider a case in which the second region is the treatment beam irradiated region 303 (see FIG. 3), and the object 301 (see FIG. 3) is included in the first region. In this case, the determining unit 210 acquires the three-dimensional position of the object 301, and determines whether the acquired three-dimensional position is included in the treatment beam irradiated region 303 using the images 510 and 520 (See FIGS. 4 and 5).

If the determining unit 210 determines that the object is not included in the first region, the controlling unit 220 controls the first radiation units 101 and 102 so as to reduce the amount of radioactive beams irradiated per unit time than when the object is included in the first region.

For example, when the object is not included in the first region, the controlling unit 220 controls to cause the radioactive beams to be irradiated at a lower frequency from one of the first radiation units 101 and 102 whose radioactive beams irradiated are not used in generating the given image than when the object is included in the first region, or controls to supply a lower current to one of the first radiation units 101 and 102 whose radioactive beams irradiated are not used in generating the given image than when the object is included in the first region.

When the determining unit 210 determines that the object is included in the second region, the controlling unit 220 controls the second radiation unit 103 to cause the second radiation unit 103 to output a treatment beam to the object.

When the object is included in the second region, the second radiation unit 103 irradiates the treatment beam 133 to the object in the body of the subject 130 (see FIG. 1). In the embodiment, the treatment beam 133 is a heavy particle beam, as an example. However, the treatment beam 133 may be an X-ray, a gamma ray, an electron beam, a proton beam, or a neutron beam, without limitation to the heavy particle beam.

The second radiation unit 103 may be fixed or movable. When the second radiation unit 103 is fixed, the object in the body of the subject 130 can be irradiated with the treatment beam 133 from the second radiation unit 103 by making the bed 104 movable.

Figure 6:
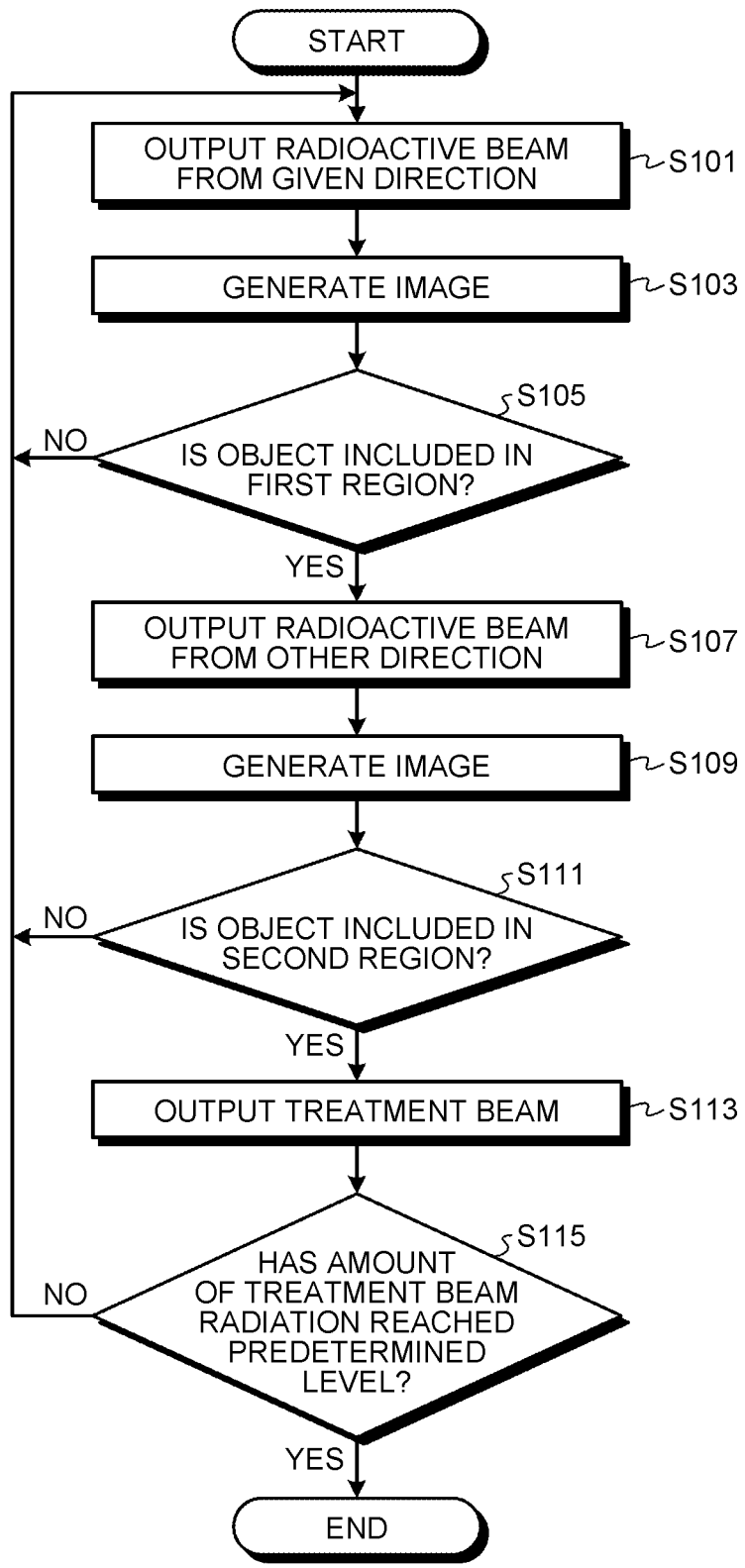
FIG. 6 is a flowchart illustrating an example of a process performed by the treatment apparatus according to the embodiment.

FIG. 6 is a flowchart illustrating an example of a process performed by the treatment apparatus 100 according to the embodiment.

To begin with, upon arrival of a first radiation unit irradiated timing at which the direction of the radioactive beams irradiated of one of the first radiation units 101 and 102 are aligned with the given direction, the controlling unit 220 instructs the first radiation unit to output the radioactive beams, and the first radiation unit irradiates the radioactive beams to the subject from the given direction (Step S101).

The first radiation unit whose radioactive beams irradiated direction are aligned with the given direction may be the first radiation unit 101 or the first radiation unit 102. Furthermore, in the embodiment, it is assumed that the first radiation unit whose radioactive beam irradiated direction are aligned with the given direction remains the same at any time, but the first radiation unit may be changed over time.

If the first radiation unit whose radioactive beams irradiated direction are aligned with the given direction is the first radiation unit 101, the detector 110 detects the radioactive beams 111 irradiated from the first radiation unit 101, and generates a fluoroscopic image of the object in the body of the subject 130 from the detected radioactive beams 111. If the first radiation unit whose radioactive beams irradiated direction are aligned with the given direction is the first radiation unit 102, the detector 120 detects the radioactive beams 122 irradiated from the first radiation unit 102, and generates a fluoroscopic image of the object in the body of the subject 130 from the detected radioactive beams 122 (Step S103).

The image generated at Step S103 serves as the given image.

Subsequently, the determining unit 210 determines whether the object is included in the first region in the given image (Step S105). If the object is not included in the first region (No at Step S105), the system control returns to Step S101.

If the object is included in the first region (Yes at Step S105), upon arrival of another first radiation unit irradiated timing at which the direction of the radioactive beams irradiated of one of the first radiation units 101 and 102 are aligned with the direction other than the given direction, the controlling unit 220 instructs the first radiation unit to output the radioactive beams, and the first radiation unit irradiates the radioactive beams to the subject from the other direction (Step S107).

Subsequently, if the first radiation unit whose radioactive beams irradiated direction are aligned with the other direction is the first radiation unit 102, the detector 120 detects the radioactive beams 122 irradiated from the first radiation unit 102, and generates a fluoroscopic image of the object in the body of the subject 130 from the detected radioactive beams 122. If the first radiation unit whose radioactive beams irradiated direction are aligned with the other direction is the first radiation unit 101, the detector 110 detects the radioactive beams 111 irradiated from the first radiation unit 101, and generates a fluoroscopic image of the object in the body of the subject 130 from the detected radioactive beams 111 (Step S109).

The determining unit 210 then determines whether the object is included in the second region based on the image generated at Step S103 (the given image) and the image generated at Step S109 (Step S111). If the object is not included in the second region (No at Step S111), the system control returns to Step S101.

If the object is included in the second region (Yes at Step S111), the controlling unit 220 instructs the second radiation unit 103 to output a certain amount of the treatment beam 133 to the object, and the second radiation unit 103 irradiates the certain amount of the treatment beam 133 to the object (Step S113).

The controlling unit 220 then determines whether the amount of the treatment beam 133 irradiated to the object has reached a predetermined level (Step S115). The predetermined level is determined by a physician or the like at a time of the pretreatment planning. If the amount of the treatment beam 133 has not reached the predetermined level (No at Step S115), the system control returns to Step S101. If the amount of the treatment beam 133 has reached the predetermined level (Yes at Step S115), the process is ended.

Figure 7:
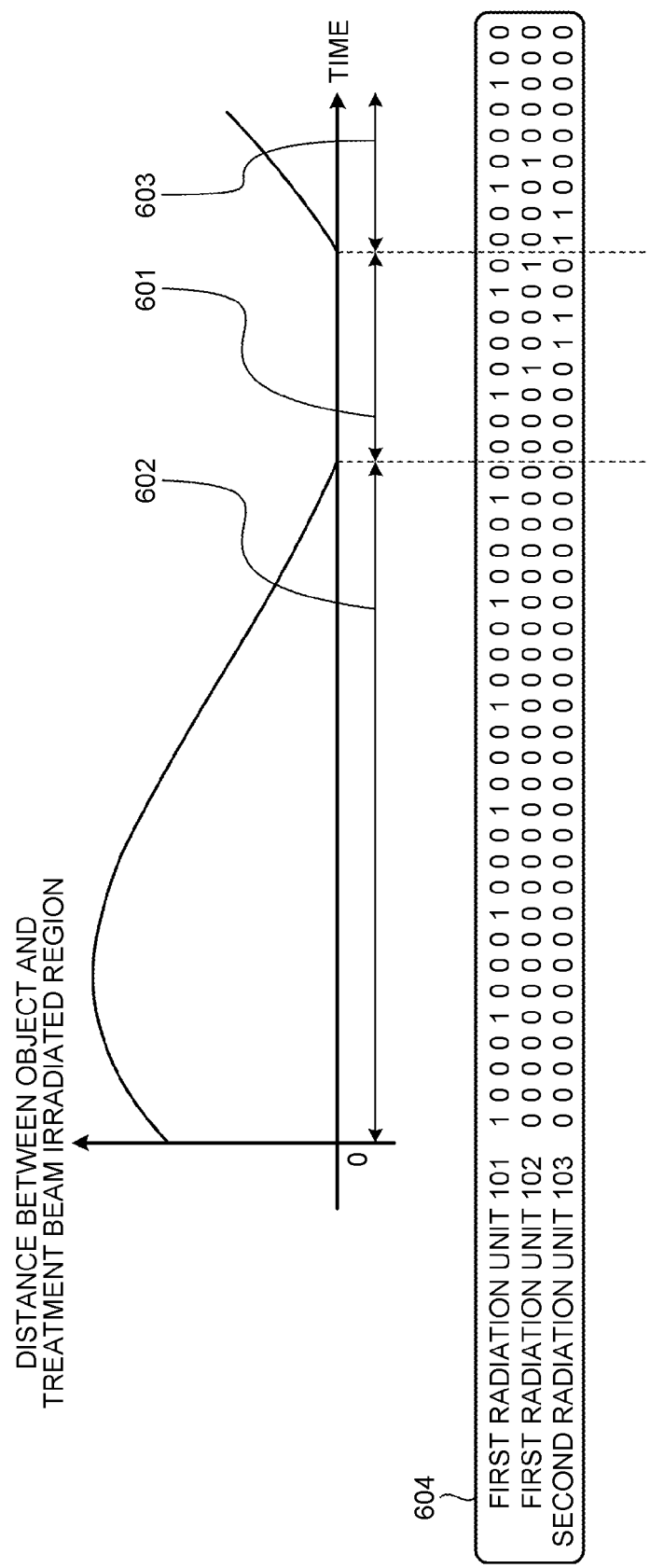
FIG. 7 is a schematic of an example of timing of radioactive beams irradiate and treatment beam irradiates with control according to the embodiment.
Figure 8:
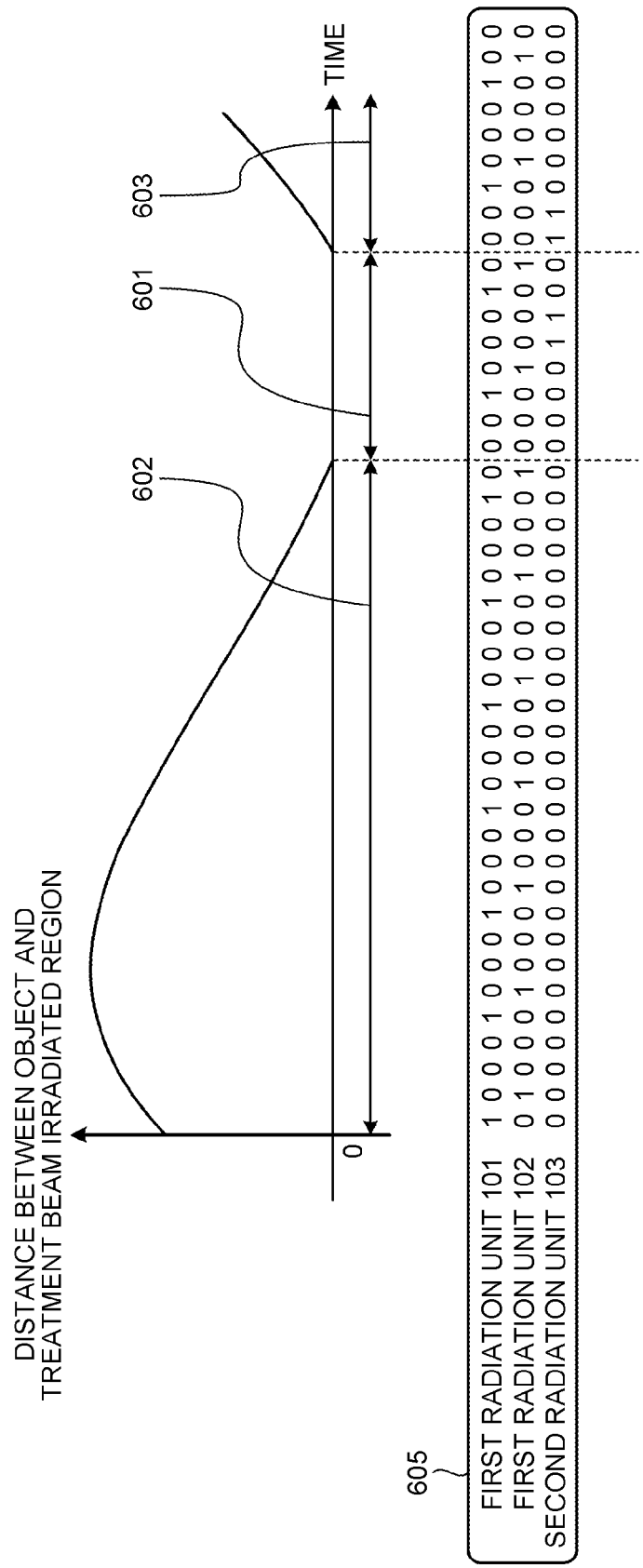
FIG. 8 is a schematic of an example of timing of radioactive beams irradiate and treatment beam irradiates without the control according to the embodiment.

FIG. 7 is a schematic of an example of timing of radioactive beams irradiate and treatment beam irradiates with the control according to the embodiment. FIG. 8 is a schematic of an example of timing of radioactive beams irradiate and treatment beam irradiates without the control according to the embodiment. In the examples illustrated in FIGS. 7 and 8, the first radiation unit whose radioactive beams irradiated direction is aligned with the given direction is the first radiation unit 101, and the first radiation unit whose radioactive beams irradiated direction is aligned with the direction other than the given direction is the first radiation unit 102.

In the examples illustrated in FIGS. 7 and 8, the horizontal axis of the graph represents the time, and the vertical axis of the graph represents the distance between the object 301 (see FIG. 3) and the treatment beam irradiated region 303 (see FIG. 3). In this example, the distance between the object 301 and the treatment beam irradiated region 303 is a distance in a three-dimensional space. When the distance is zero, the object 301 is included in the treatment beam irradiated region 303.

In other words, a period 601 in which the distance between the object 301 and the treatment beam irradiated region 303 is zero is a gating ON period during which an irradiation of the treatment beam 133 is permitted, and the periods 602 and 603 in which the distance between the object 301 and the treatment beam irradiated region 303 is more than zero is a gating OFF period during which an irradiation of the treatment beam 133 is not permitted.

In the control 604 according to the embodiment illustrated in FIG. 7 and the conventional control 605 illustrated in FIG. 8, "1" represents radioactive beams irradiated at the corresponding time, and "0" represents no radioactive beams irradiated at the corresponding time. In the examples illustrated in FIGS. 7 and 8, in order to prevent noise in the image 510 (see FIG. 4) resulting from scattered radioactive beams 111 or to prevent noise in the image 520 (see FIG. 5) resulting from scattered radioactive beams 122, the radioactive beams 111 are irradiated from the first radiation unit 101 at a different timing from the radioactive beams 122 irradiated from the first radiation unit 102.

In the example illustrated in FIG. 7, with the control 604 according to the embodiment, because the object 301 is not included in the projected region 513 that is the first region (see FIG. 4) during the periods 602 and 603, the radioactive beams are irradiated from the first radiation unit 102 at a lower frequency than with the conventional control 605 illustrated in FIG. 8.

In the example illustrated in FIG. 7 with the control 604 according to the embodiment, the timing at which the treatment beam 133 is irradiated from the second radiation unit 103 is the same as that in the example illustrated in FIG. 8 in which the conventional control 605 is performed.

In the manner described above, according to the embodiment, because the frequency of radioactive beams irradiates can be reduced without changing the treatment beam irradiates, the amount of exposure of the subject 130 to the fluoroscopic radioactive beams can be further reduced.

Furthermore, in the embodiment, because the given direction is fixed, and the first radiation unit whose radioactive beams irradiated direction are aligned with the given direction remains the same all the time, the size of the target region to be searched to keep track of the object can be reduced, so that the computation resources for keeping track of the object can be reduced.

For example, when the given direction is fixed to the direction of the radioactive beams 111 irradiated, the time interval between the images 510 generated based on the radioactive beams 111 are one half of that when the given direction is switched alternatingly between the direction of the radioactive beams 111 irradiated and the direction of the radioactive beams 122 irradiated. When the time interval is one half, the distance by which the object image 511 moves during this period becomes reduced. Therefore, the size of the target region to be searched to keep track of the object image 511 can be reduced, so that the computation resources for keeping track of the object image 511 can be reduced.

First Modification

Explained in a first modification is an example in which an enlargement of the projection of the second region on the given image is used as the first region.

Figure 9:
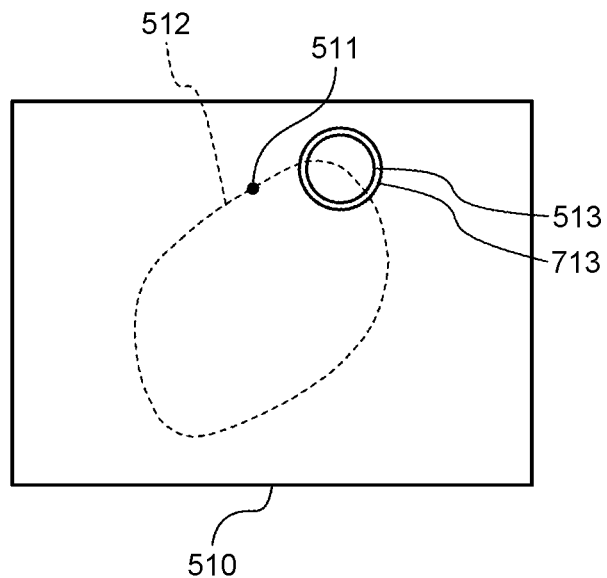
FIG. 9 is a schematic illustrating an image generated by a detector according to a first modification.

FIG. 9 is a schematic of an example of the image 510 generated by the detector 110 according to the first modification. The image 510 includes the object image 511 that is a projection of the object 301 (see FIG. 3) on the detection surface of the detector 110 in the direction of the radioactive beams 111 irradiated. The projected trajectory 512 is a projection of the trajectory 302 (see FIG. 3) on the image 510, and the projected region 513 is a projection of the treatment beam irradiated region 303 (see FIG. 3) on the image 510. An enlarged region 713 is an enlargement (expansion) of the projected region 513.

Figure 10:
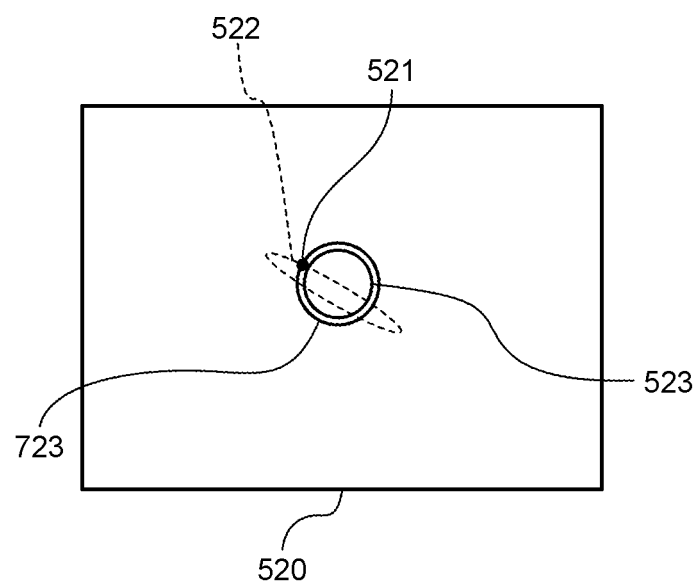
FIG. 10 is a schematic illustrating an image generated by another detector according to the first modification.

FIG. 10 is a schematic of an example of the image 520 generated by the detector 120 according to the first modification. The image 520 includes the object image 521 that is a projection of the object 301 (see FIG. 3) on the detection surface of the detector 120 in the direction of the radioactive beams 122 irradiated. The projected trajectory 522 is a projection of the trajectory 302 (see FIG. 3) on the image 520, the projected region 523 is a projection of the treatment beam irradiated region 303 (see FIG. 3) on the image 520. An enlarged region 723 is an enlargement (expansion) of the projected region 523.

In this example, when the image 510 is the given image (that is, when the direction of the radioactive beams 111 irradiated are the given direction), the enlarged region 713 corresponds to the first region. When the image 520 is the given image (that is, when the direction of the radioactive beams 122 irradiated are the given direction), the enlarged region 723 corresponds to the first region.

In this manner, the image from the other direction is also generated in addition to that from the given direction from time slightly before the object 301 enters the treatment beam irradiated region 303. Therefore, it becomes possible to determine whether to set the gating to ON, using these images captured from a plurality of directions. The first modification is useful when it is necessary to determine whether to switch the gating from OFF to ON.

Second Modification

In a second modification, the first region is a region resulting from removing an internal region included in the projected region from an enlargement of the projected region that is a projection of the second region is the given image.

Figure 11:
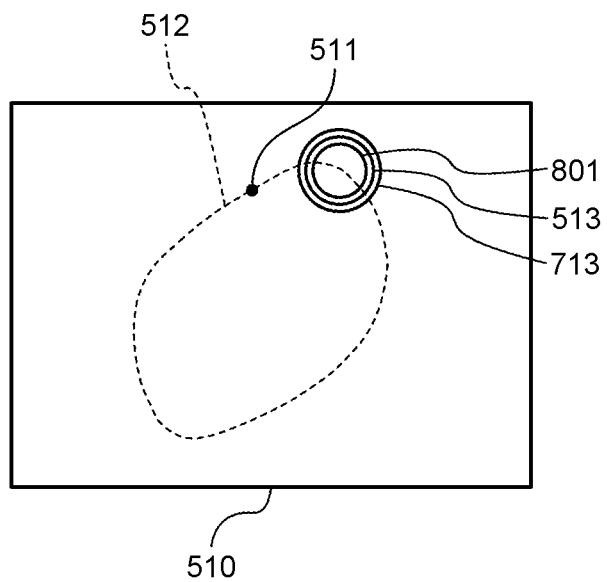
FIG. 11 is a schematic illustrating an image generated by a detector according to a second modification.

FIG. 11 is a schematic of an example of the image 510 generated by the detector 110 according to a second modification. The image 510 includes the object image 511 that is a projection of the object 301 (see FIG. 3) on the detection surface of the detector 110 in the direction of the radioactive beams 111 irradiated. The projected trajectory 512 is a projection of the trajectory 302 (see FIG. 3) on the image 510, and the projected region 513 (see FIG. 3) is a projection of the treatment beam irradiated region 303 on the image 510. The enlarged region 713 is an enlargement (expansion) of the projected region 513, and an internal region 801 is a region included in the projected region 513.

Figure 12:
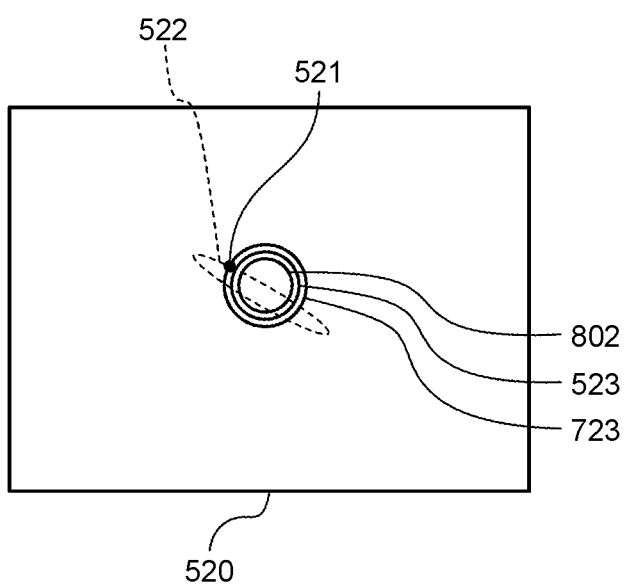
FIG. 12 is a schematic illustrating an image generated by another detector according to a second modification.

FIG. 12 is a schematic of an example of the image 520 generated by the detector 120 according to the second modification. The image 520 includes the object image 521 that is a projection of the object 301 (see FIG. 3) on the detection surface of the detector 120 in the direction of the radioactive beams 122 irradiated. The projected trajectory 522 is a projection of the trajectory 302 (see FIG. 3) on the image 520, and the projected region 523 is a projection of the treatment beam irradiated region 303 (see FIG. 3) on the image 520. The enlarged region 723 is an enlargement (expansion) of the projected region 523, and an internal region 802 is a region included in the projected region 523.

In this example, when the image 510 is the given image (that is, when the direction of the radioactive beams 111 irradiated are the given direction), the first region corresponds to a region resulting from removing the internal region 801 from the enlarged region 713. When the image 520 is the given image (that is, when the direction of the radioactive beams 122 irradiated are the given direction), the first region corresponds to a region resulting from removing the internal region 802 from the enlarged region 723.

In this manner, the image from the other direction is also generated in addition to the image from the given direction, from the time slightly before the object 301 enters the treatment beam irradiated region 303 and from the time slightly before the object 301 exits the treatment beam irradiated region 303, so that it becomes possible to determine whether to set the gating ON and whether to set the gating OFF using images captured from a plurality of directions. The second modification is useful when it is necessary to determine whether to switch the gating from OFF to ON and to switch the gating from ON to OFF, and enables the amount of exposure of the subject 130 to the fluoroscopic radioactive beams to be further reduced.

Third Modification

Explained in the third modification is an example in which it is determined whether the object is included in the first region by estimating the position of the object in the given image at each time increment in the second modification.

In this example, the determining unit 210 estimates the position of the object in the given image at each time increment, and determines that the object is included in the first region at a time increment at which the estimated position is included in the first position, and determines that the object is not included in the first region at a time increment at which the estimated position is not included in the first region.

Any method can be used to estimate the position of the object at each time increment. For example, with an assumption that the cycle or trajectory of a current respiration is the same as those of the past, the time at which the position of the object is included in the first region and the time at which the position of the object is not included in the first region can be estimated from the phase of the current respiration.

In the third modification as well as in the second modification, when the object is not included in the first region, the controlling unit 220 controls to cause a radioactive beams to be irradiated at a lower frequency from one of the first radiation units 101 and 102 whose radioactive beams irradiated are not used in generating the given image than when the object is included in the first region, or controls to supply a lower current to one of the first radiation units 101 and 102 whose radioactive beams irradiated are not used in generating the given image than when the object is included in the first region. In other words, the controlling unit 220 controls the first radiation units 101 and 102 to output a smaller amount of radioactive beams per unit time than when the object is included in the first region.

This control allows the position of the object 301 to be recognized without being affected near the time at which the gating is switched from OFF to ON and near the time at which the gating is switched from ON to OFF, despite the frame rate or the image quality of the given image may be reduced.

The third modification is useful when it is necessary to determine whether to switch the gating from OFF to ON and whether to switch the gating from ON to OFF, and can further reduce the amount of exposure of the subject 130 to the fluoroscopic radioactive beams.

Fourth Modification

Explained in a fourth modification is an example in which one of the directions of the radioactive beams irradiates resulting in a larger trajectory of the object movement than in any other direction is used as the given direction. The direction resulting in a larger trajectory of the movement is a direction from which the object image with a wider area of blurriness caused by movement is captured.

For example, when the image 510 illustrated in FIG. 4 is compared with the image 520 illustrated in FIG. 5, the projected trajectory 512 in the image 510 is larger than the projected trajectory 522 in the image 520, and the trajectory of the object 301 shown in a larger size in the image 510. Therefore, the direction of the radioactive beams 111 radiation are used as the given direction.

The controlling unit 220 may perform the control for determining one of the directions of the radioactive beams irradiate resulting in a larger trajectory of the object movement than in any other direction as the given direction using images generated at a time of the treatment planning or generated in the past treatment. The image may be moving images or still images. Examples of moving images include a four-dimensional computed tomographic (4DCT) movie and an X-ray movie captured from more than two directions. The past treatment includes treatment performed on an earlier date, or a prior treatment performed on the same day.

In this manner, it is possible to monitor or to keep track of the main two-dimensional movement in the three-dimensional movement of the object 301. Furthermore, the object image 511 is included in the projected region 513 over a shorter time period than the time period over which the object image 520 is included in the projected region 523. Therefore, the subject 130 is less exposed to the fluoroscopic radioactive beams when used as the given direction is one of the directions of the radioactive beams irradiate resulting in a larger trajectory of the object movement than in any other direction.

Fifth Modification

In the fifth modification, the controlling unit 220 controls at least one of positions of the first radiation units 101 and 102, the positions of the detectors 110 and 120, and the position of the bed 104 on which the subject laid down so as to align a direction from one of the first radiation units 101 and 102 to the subject with the given direction.

More specifically, the controlling unit 220 controls at least one of the positions of the first radiation units 101 and 102, the positions of the detectors 110 and 120, and the position of the bed 104 on which the subject laid down so that the direction from one of the first radiation units 101 and 102 to the subject is aligned with one of the directions of the radioactive beams irradiate resulting in a larger resultant trajectory of the object movement.

As explained in the fourth modification, the controlling unit 220 can determine which one of the directions of the radioactive beams irradiated results in a larger object movement trajectory using images generated during the treatment planning or in the past treatment, for example. Hence, the controlling unit 220 can control at least one of the positions of the first radiation units 101 and 102, the positions of the detectors 110 and 120, and the position of the bed 104 on which the subject laid down to align the direction from one of the first radiation units 101 and 102 to the subject with the determined direction.

In this manner, it becomes possible to monitor or to keep track of the main two-dimensional movement in the three-dimensional movement of the object 301. Furthermore, the object image 511 is included in the projected region 513 over a shorter time period than that over which the object image 520 is included in the projected region 523. Therefore, the subject 130 is less exposed to the fluoroscopic radioactive beams when used as the given direction is one of the directions of the radioactive beams irradiates resulting in a larger trajectory of the object movement than in any other direction.

Sixth Modification

Explained in a sixth modification is an example in which the determining unit 210 further determines if the object is included in the second region using an external sensor, and if object is not included in the second region, the controlling unit 220 controls the first radiation units 101 and 102 not to output the radioactive beams. By using a detection result of the external sensor, the movement of the object caused by the body movement, respirations, cardiac beats, and the like can be estimated highly accurately. A distance sensor, a pulse sensor, a pressure sensor, an infrared marker, an infrared camera, a respiration sensor, an ultrasonic sensor, or the like may be used as the external sensor.

For example, when the affected area is near one of the lungs, the movement of the affected area is mainly caused by respirations. Respirations can be monitored using an infrared marker and an infrared camera placed on the abdominal area, or using a respiration sensor. Ultrasonic images may be often used in monitoring the movement, regardless of the position of the affected area. The body movement and the pulse may also be monitored with these sensors.

The determining unit 210 then estimates the position of the object using a model formula for estimating the position of the object generated in advance, based on the information from these external sensors. If it is less likely for the estimated position of the object to be included in the second region, the controlling unit 220 controls the first radiation units 101 and 102 so as not to output their radioactive beams.

In this manner, the amount of exposure of the subject 130 to the fluoroscopic radioactive beams can be further reduced.

Hardware Configuration

Figure 13:
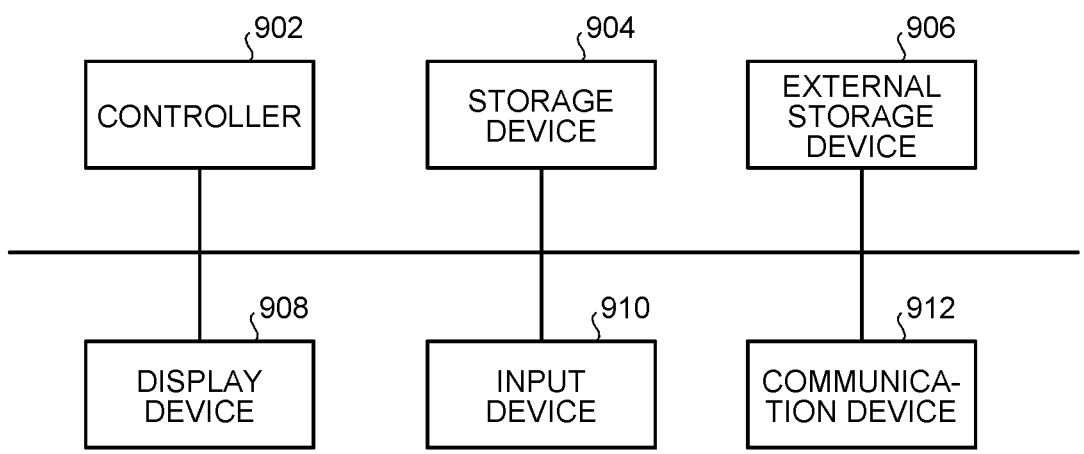
FIG. 13 is a schematic illustrating an example of a hardware configuration of the treatment apparatus according to the embodiment and the modifications.

FIG. 13 is a block diagram illustrating an example of a hardware configuration of the treatment apparatus 100 (the controller 200) according to the embodiment and the modifications described above. As illustrated in FIG. 13, the treatment apparatus 100 according to the embodiment and the modifications includes a controller 902 such as a dedicated chip, a field programmable gate array (FPGA), or a central processing unit (CPU), a storage device 904 such as a read-only memory (ROM) and a random access memory (RAM), an external storage device 906 such as a hard disk drive (HDD) or a solid state drive (SSD), a display device 908, input devices 910 such as a mouse and a keyboard, and a communication interface (I/F) 912, and can be implemented with a hardware configuration that uses a general computer.

The computer program executed on the treatment apparatus 100 according to the embodiment and the modifications is provided in a manner incorporated in the ROM or the like in advance. The computer program executed on the treatment apparatus 100 according to the embodiment and the modifications may also be provided in a manner recorded in a computer-readable recording medium such as a compact disc read-only memory (CD-ROM), a compact disc recordable (CD-R), a memory card, a digital versatile disc (DVD), or a flexible disk (FD) as an installable or executable file. The computer program executed on the treatment apparatus 100 according to the embodiment and the modifications may also be stored in a computer connected to a network such as the Internet, and may be made available for download over the network.

The computer program executed on the treatment apparatus 100 according to the embodiment and the modifications has a modular structure for allowing a computer to implement each of the units described above. In the actual hardware, for example, the controller 902 reads the computer program from the external storage device 906 onto the storage device 904, and executes the computer program to implement each of the units described above on the computer.

In the manner described above, according to the embodiment and the modifications, the amount of exposure to the fluoroscopic radioactive beams can be further reduced.

For example, the steps in the flowchart according to the embodiment may be executed in a different order, or some of the steps may be executed simultaneously as long as such a modification is not against the nature of the process. The steps may also be executed in a different order every time the process is executed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A treatment system comprising:
a plurality of first radiators each configured to irradiate a radioactive beam to a subject;
a plurality of detectors each configured to detect a radioactive beam transmitted through the subject; and
a controller comprising circuitry, the controller being configured to:
obtain a first region by projecting a second region onto a first image generated using a radioactive beam detected by a detector that is one of the plurality of detectors;
determine whether an object in the subject is included in the first region; and
control the first radiators so that, when the object is determined not to be included in the first region, a smaller amount of radioactive beams is irradiated per unit time than when the object is determined to be included in the first region.

2. The system according to claim 1, further comprising a second radiator configured to irradiate a treatment beam, wherein
the controller is configured to, when the object is determined to be included in the first region, further determine whether the object is included in the second region using one or more images other than the first image generated using radioactive beams transmitted through the subject detected by the detectors, and
the controller is configured to, when the object is determined to be included in the second region, control the second radiator to irradiate the treatment beam to the object.

3. The system according to claim 2, wherein
the controller is configured to determine whether the object is included in the second region using an external sensor, and
the controller is configured to control the first radiators so as not to irradiate the radioactive beams when the object is determined not to be included in the second region.

4. The system according to claim 2, wherein the controller is configured to obtain the first region by enlarging a region resulting from projecting the second region onto the first image.

5. The system according to claim 2, wherein the controller is configured to obtain the first region by removing a region included in an enlargement of a region resulting from projecting the second region onto the first image.

6. The system according to claim 5, wherein the controller is configured to estimate a position of the object in the first image at each of a plurality of different times, determine that the object is included in the first region at times when the estimated position is included in the first region, and determine that the object is not included in the first region at times when the estimated position is not included in the first region.

7. The system according to claim 1, wherein the controller is configured to determine that the object is included in the first region when the object is included in the first region in the first image, and to determine that the object is not included in the first region when the object is not included in the first region in the first image.

8. The system according to claim 1, wherein, the controller is configured to, when the object is determined not to be included in the first region, cause a radioactive beam to be irradiated at a lower frequency from any of the first radiators whose radioactive beam irradiated is not used in generating the first image, or to supply a lower current to the any of the first radiators than when the object is determined to be included in the first region.

9. The system according to claim 1, wherein the object is a marker indwelling in or near an affected area of the subject.

10. The system according to claim 1, wherein the radioactive beam used to generate the first image is irradiated from a given direction.

11. The system according to claim 10, wherein the given direction is fixed.

12. The system according to claim 10, wherein the given direction corresponds to a direction of irradiating the radioactive beam resulting in a larger trajectory of movement of the object than any other direction.

13. The system according to claim 12, wherein the controller is configured to determine the given direction based on an image generated at a time of treatment planning or in a past treatment.

14. The system according to claim 10, wherein the controller is configured to control at least one of a position of one of the first radiators, a position of a corresponding detector, and a position of a bed so that a direction from the one of the first radiators to the subject is aligned with the given direction.

15. A control device comprising:
a processor; and
a memory configured to store processor-executable instructions that, when executed by the processor, cause the processor to:
obtain a first region by projecting a second region onto a first image generated using a detected radioactive beam transmitted through a subject;
determine whether an object in the subject is included in the first region; and
control a plurality of first radiators so that, when the object is determined not to be included in the first region, a smaller amount of radioactive beams is irradiated per unit time than when the object is determined to be included in the first region.

16. The device according to claim 15, wherein when the object is determined to be included in the first region, the determining further determines whether the object is included in the second region using one or more images other than the first image generated using detected radioactive beams transmitted through the subject, and when the object is determined to be included in the second region, the controlling further controls a second radiator to cause the second radiator to irradiate a treatment beam to the object.

17. A treatment method executed on a treatment system including a plurality of first radiators each configured to irradiate a radioactive beam to a subject, and a plurality of detectors each configured to detect a radioactive beam transmitted through the subject, the method comprising:

obtaining a first region by projecting a second region onto a first image generated using a radioactive beam detected by a detector that is one of the plurality of detectors;

determining whether an object in the subject is included in the first region; and controlling the first radiators so that, when the object is determined not to be included in the first region, a smaller amount of radioactive beams is irradiated per unit time than when the object is determined to be included in the first region.

* * * * *